United States Patent
Wilander et al.

(10) Patent No.: US 7,980,754 B2
(45) Date of Patent: Jul. 19, 2011

(54) METHOD FOR BRINGING A POWDER AND A LIQUID COMPONENT IN CONTACT WITH EACH OTHER FOR MIXING TO FORM BONE CEMENT

(75) Inventors: Lars Wilander, Körsbärsliden (SE); Steen Stavnshöj, Fuxgatan (SE)

(73) Assignee: Biomet Cementing Technologies AB, Sjobo (SE)

( * ) Notice: Subject to any disclaimer, the term of this patent is extended or adjusted under 35 U.S.C. 154(b) by 1696 days.

(21) Appl. No.: 11/194,994

(22) Filed: Aug. 2, 2005

(65) Prior Publication Data
US 2007/0016215 A1    Jan. 18, 2007

(30) Foreign Application Priority Data
Jul. 5, 2005 (SE) .................................... 0501552

(51) Int. Cl.
*B01F 13/06* (2006.01)
(52) U.S. Cl. ........ 366/139; 366/163.1; 604/88; 206/222
(58) Field of Classification Search .................. 366/139, 366/163.1, 189; 604/86, 88; 206/222
See application file for complete search history.

(56) References Cited

U.S. PATENT DOCUMENTS
| | | | |
|---|---|---|---|
| 4,973,168 A | 11/1990 | Chan | |
| 5,328,262 A | 7/1994 | Lidgren et al. | |
| 6,572,256 B2 * | 6/2003 | Seaton et al. | 366/139 |
| 2002/0043542 A1 | 4/2002 | Chan | |
| 2004/0066706 A1 | 4/2004 | Barker et al. | |

FOREIGN PATENT DOCUMENTS
| | | |
|---|---|---|
| DE | 43 02 230 A1 | 8/1993 |
| DE | 19709036 | 9/1998 |
| WO | WO/96/07472 A1 | 3/1996 |

* cited by examiner

*Primary Examiner* — David L Sorkin
(74) *Attorney, Agent, or Firm* — Tarolli, Sundheim, Covell & Tummino LLP

(57) ABSTRACT

The present invention relates to a method for bringing a powder and a liquid component, preferably polymer and monomer, in contact with each other for mixing thereof, preferably to form bone cement, wherein the powder component (P) is placed in a mixing container (1) in which the mixing shall occur and the liquid component (M) in a liquid container (18) from which said the liquid component (M) is transferred to the powder component (P) in the mixing container (1). In this method, a vacuum is generated in the mixing container (1) and the liquid container (18) is opened by means of at least one cannula (14) or similar member through which the liquid component (M) can be brought to flow from the liquid container (18) to the mixing container (1). The vacuum is brought to suck the liquid component (M) from the liquid container (18), through the cannula (14) and into the mixing container (1) to the powder component (P) therein, and/or is the liquid component (M) pressed into the mixing container (1) through the cannula (14) while the liquid container (18) is compressed because of the pressure difference between the vacuum in the interior of the liquid container (18) and the air pressure outside the liquid container. The invention also relates to a device for carrying through the method.

24 Claims, 5 Drawing Sheets

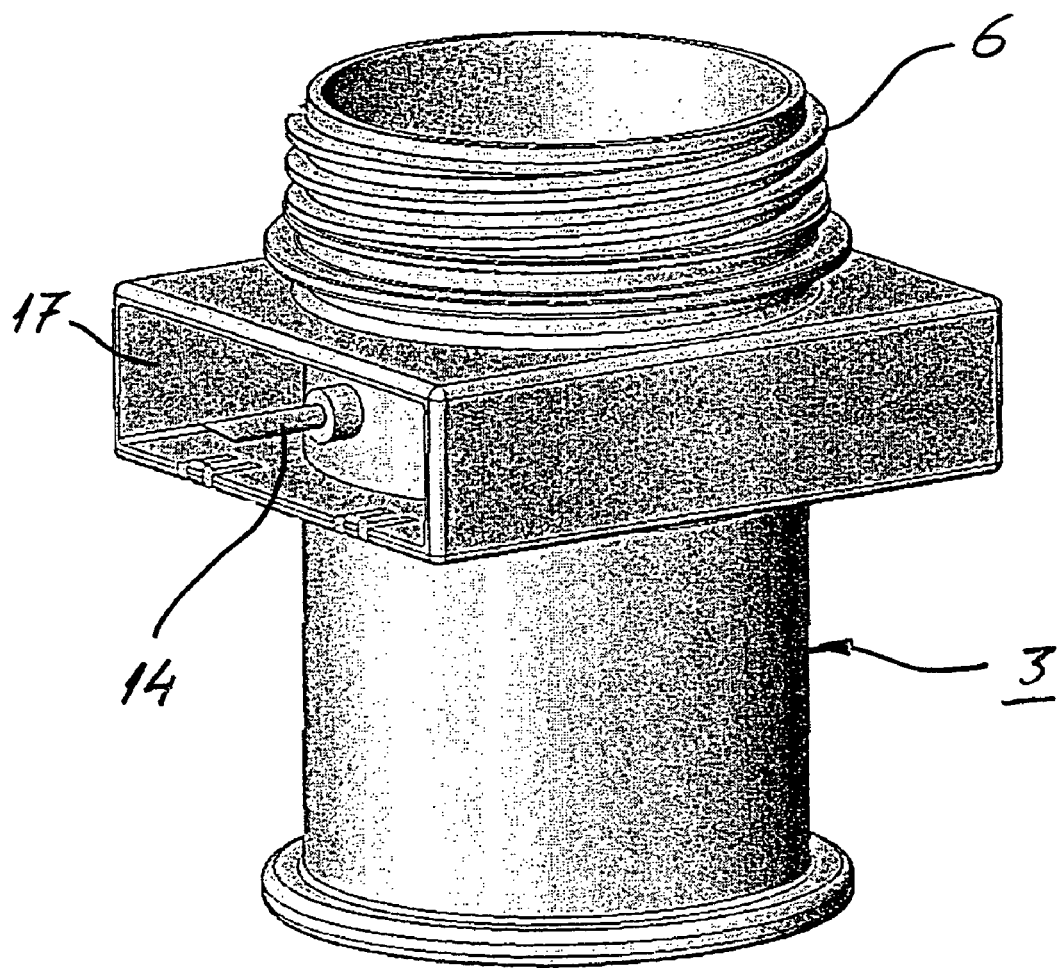

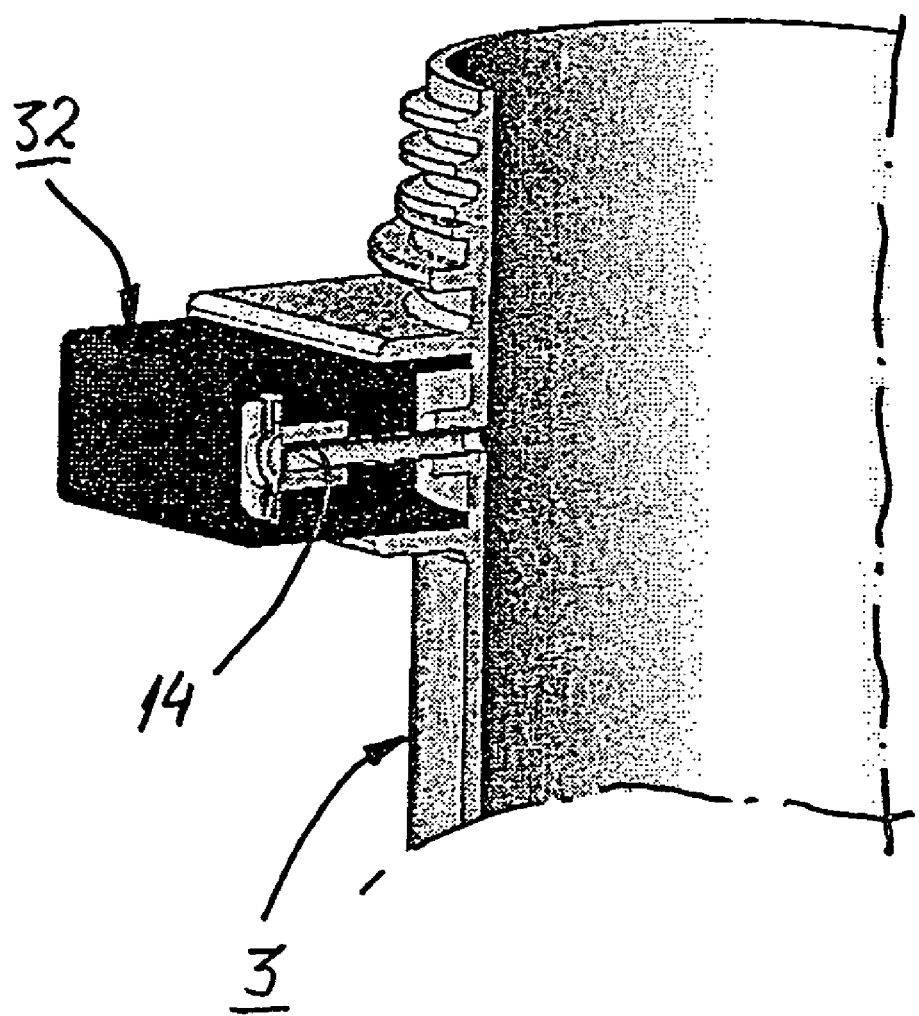

METHOD FOR BRINGING A POWDER AND A LIQUID COMPONENT IN CONTACT WITH EACH OTHER FOR MIXING TO FORM BONE CEMENT

FIELD OF THE INVENTION

The present invention relates to a method and a device for bringing a powder and a liquid component, preferably polymer and monomer, in contact with each other for mixing thereof, preferably to form bone cement, wherein the powder component is placed in a mixing container in which the mixing shall occur and the liquid component in a liquid container from which said liquid component is transferred to the powder component in the mixing container.

BACKGROUND OF THE INVENTION

Mixing devices for mixing polymer and monomer for production of bone cement are already known from U.S. Pat. No. 5,328,262 and U.S. Pat. No. 4,973,168. At the device of U.S. Pat. No. 5,328,262, there is polymer in the mixing container and monomer is poured into the mixing container from a liquid container. Then, polymer and monomer are mixed under a vacuum and after mixing, the bone cement is collected under a vacuum for subsequent discharge. At the device of U.S. Pat. No. 4,973,168, there is polymer in the mixing container and monomer in a syringe with a cannula. This cannula is used for puncturing a membrane in the mixing container, whereafter monomer is injected into the mixing container.

It has been noticed that the device and method of U.S. Pat. No. 4,973,168 for adding monomer to polymer do not meet the present demands for quick and effective distribution of the monomer in the polymer for producing bone cement with the required properties.

SUMMARY OF THE INVENTION

The object of the present invention is to provide a method and a device to remedy the abovementioned drawbacks. This is arrived at according to the invention by means of the characterizing features of primarily subsequent claims 1 and 15.

By using a cannula for opening the liquid container and while monomer through said cannula is transferred to the mixing container by being sucked thereinto by vacuum and/or pressed thereinto by pressure differences between the interior and exterior of the liquid container, a simple method and a simple device are obtained, which provide for a sufficiently quick and effective distribution of the monomer in the polymer.

BRIEF DESCRIPTION OF THE DRAWINGS

The invention will be further described below with reference to the accompanying drawings, in which:

FIG. 4 is a perspective view of a container member of the device of FIG. 1; and

FIG. 5 illustrates parts of the container member of FIG. 4 having a closing device.

DESCRIPTION OF EXAMPLE EMBODIMENTS

Figure 1:
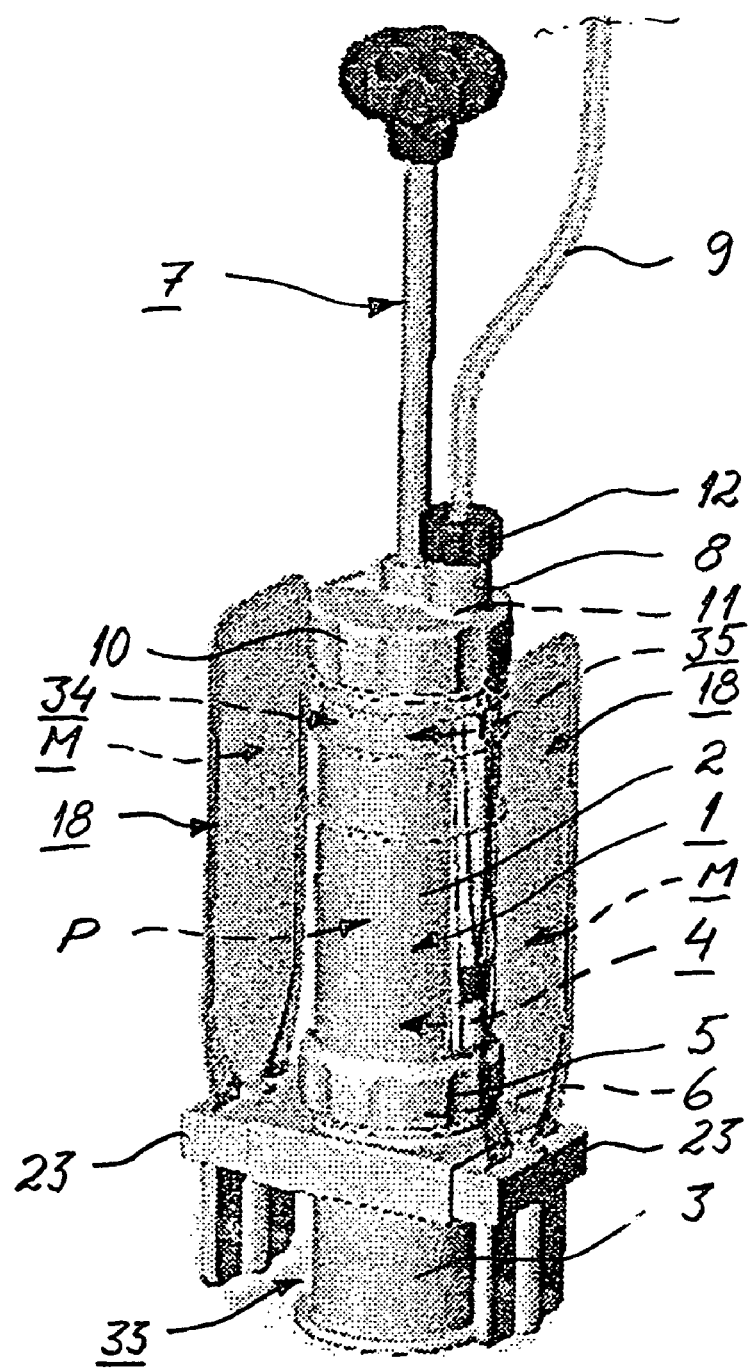
FIG. 1 is a perspective view of a device according to the invention.
Figure 2:
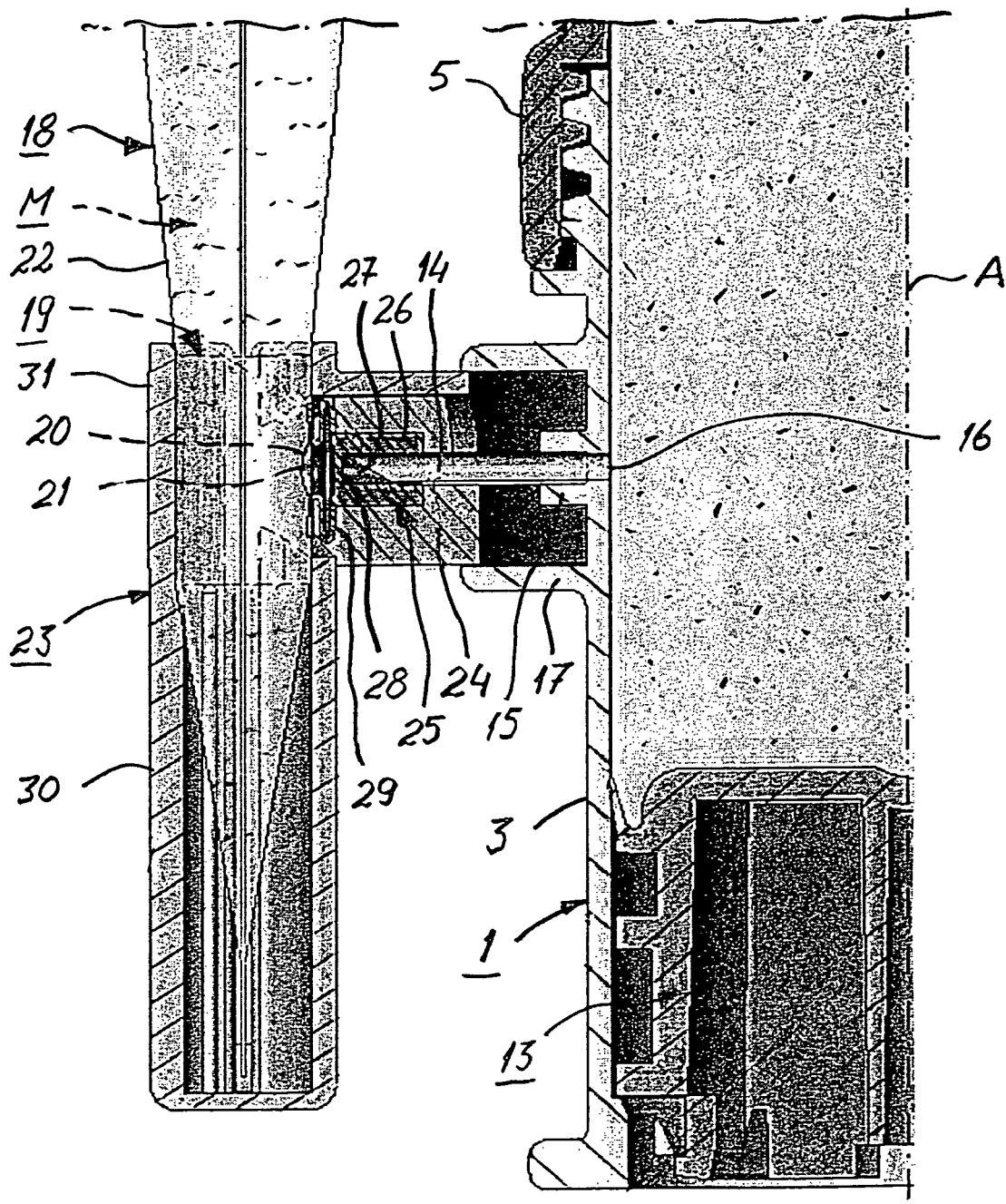
FIG. 2 is a section through a part of the device of FIG. 1.

The mixing container 1 illustrated in the drawings is adapted for mixing a powder component in the form of polymer P and a liquid component in the form of monomer M, for production of bone cement. The mixing container 1 may e.g. consist of a first container member 2 and a second container member 3 which are closely connectable to each other for defining a common mixing space 4. The container members 2, 3 may be connected to each other by screwing a threaded part 5 on the first member 2 onto a threaded part 6 on the second member 3. Hereby, the container members 2, 3 can be drawn together until they engage each other closely, eventually through a sealing ring (not shown).

The first container member 2 may consist of a previously known member with a mixing means 7 and a connecting member 8 which through a hose 9 or similar can be connected to a vacuum pump (not shown). The mixing means 7 and the connecting member 8 are in this embodiment provided in a cap 10 which is screwed onto the first container member 2. At the illustrated embodiment, the mixing means 7 has at an inner end a transverse mixing part (not shown) and it can be moved up and down and rotated relative to the mixing container 1 for mixing therein.

In the cap 10 or at any other suitable location there may be provided a filter 11 for letting through only gases to the vacuum pump.

A plug 12 may be provided on the connecting member 8 and screwed off such that a discharge nozzle (not shown) can be mounted on the connecting member 8 instead of the hose 9 when necessary.

The second container member 3 has a piston 13 which is closely provided in a first end portion of the mixing container 1, here the second container member 3, and which in a manner known per se can be fixedly attached to the second container member 3 when required and releasable therefrom when necessary. At a distance from the piston 13 and on two opposite sides of the second container member 3, there are provided two cannulae 14 which protrude radially outwards from said second container member relative to a geometric longitudinal axis A thereto. These cannulae 14 may be pressed onto sleeves 15 which protrude radially from the container sides and which communicate with the mixing space 4 through holes 16 in the container sides. The container sides may also have guide sleeves 17 which protrude in a radial direction therefrom such that each cannula 14 will be located in such a guide sleeve 17.

The liquid monomer M is situated in two sealed liquid containers 18. Each liquid container 18 may have an inner tube member 19 with a lateral hole 20 which is closed by a wall portion 21 of the wall 22 of the liquid container 18. The liquid containers 18 can be placed in brackets 23 which hold said containers in positions ready for use relative to the cannulae 14.

Each bracket 23 has a guide pin 24 which protrudes in a lateral direction from the bracket 23 and which is displaceably mounted in the guide sleeve 17 such that the bracket 23 can be displaced towards the cannula 14. The brackets 23 may be mounted on the guide sleeves 17 such that they normally do not loosen from said sleeves 17.

In the guide pin 24 there is provided a sealing means 25 having a sleeve 26 with a hole 27 which is engaged by the cannula 14 such that the sleeve 26 closely engages said cannula 14. The hole 27 in the sleeve 26 has a wall 28 which closes said hole 27 at an outer side of the cannula 14. The wall 28 is adapted to prevent air from entering the mixing space 4. The wall 28 can be opened by the cannula 14 by pressing it against said cannula 14 when the liquid container 18 is pressed thereagainst.

At the front, the sleeve 26 is provided with a bellows-like sealing member 29 which closely engages the wall 22 of the liquid container 18 around the wall portion 21 within which the lateral hole 20 of the inner tube member 19 is situated and which is to be penetrated by the cannula 14.

At the embodiment shown, the bracket 23 comprises an upwards open sleeve 30 which at the top has a retaining member 31 which is designed to hold the liquid container 18 in such a ready position relative to the cannula 14 that the wall portion 21 thereof, which is to be opened by said cannula 14, will be located substantially opposite thereto. At the illustrated embodiment, the retaining member 31 is designed to hold that part of the liquid container 18 in which the inner tube member 19 is situated, in said ready position.

If the mixing container 1 comprises two cannulae 14 and if only one liquid container 18 shall be emptied therein, there may be a cap 32 (see FIG. 5) which can be placed on the mixing container 1 at the cannula 14 which is not used, such that said cap 32, inter alia, covers said cannula 14 and for preventing the sealing means 25 at that cannula from loosening.

Figure 3:
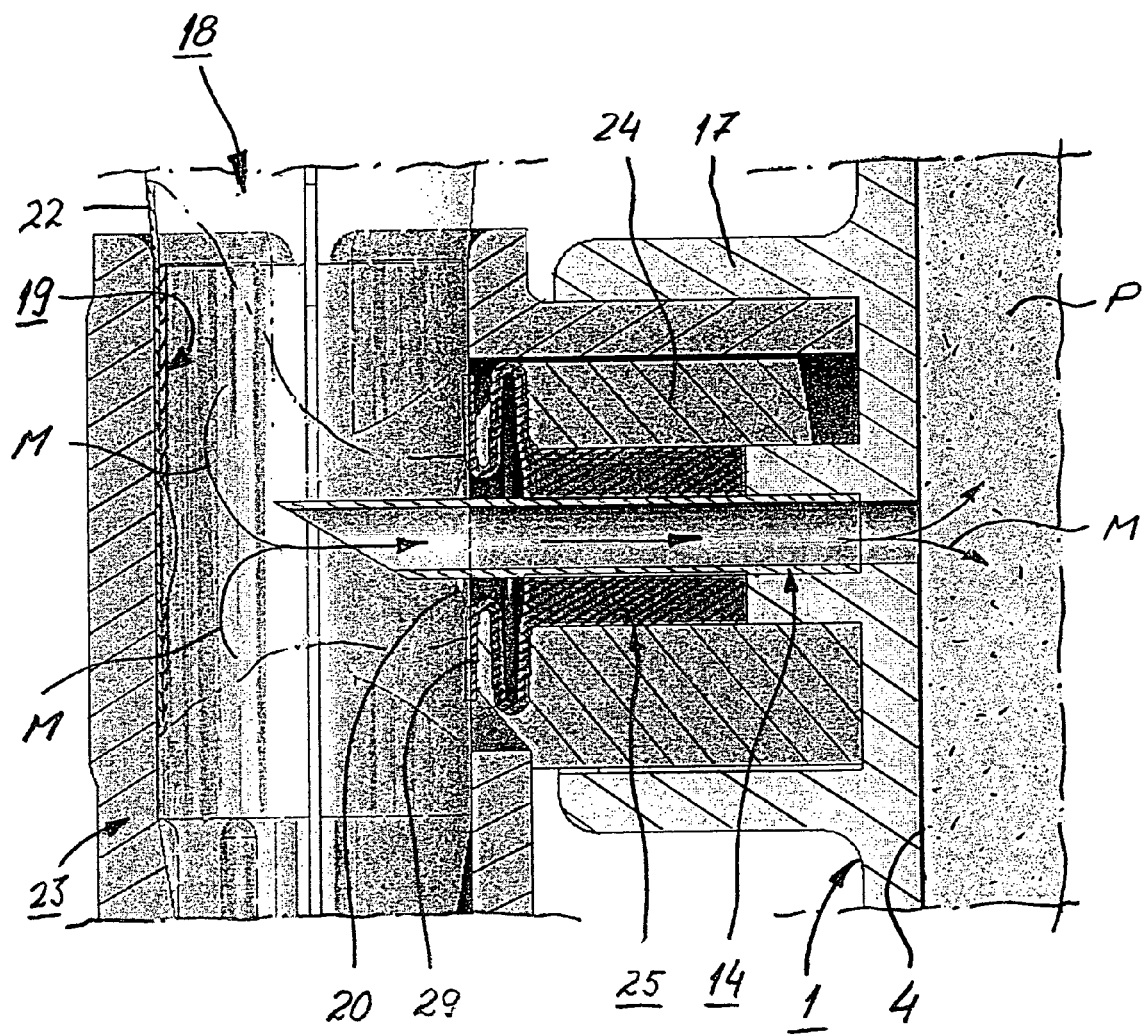
FIG. 3 is a section through a part of the device of FIG. 2.

In order to produce bone cement, the vacuum pump is started for generating a vacuum in the mixing container 1. By vacuum is here meant a substantial negative pressure of e.g. about −0.87 bar. When this or another required vacuum has been generated in the mixing container 1, the brackets 23 are pressed, preferably substantially at the same time, in the direction towards the cannulae 14 which penetrate the wall portions 21 of the liquid containers 18, and the cannulae 14 will then protrude into the inner tube members 19 (see FIG. 3). Since the cannulae 14 thus have opened the liquid containers 18, connection is obtained between the mixing space 4 and the liquid containers 18 through the cannulae 14 and the vacuum in the mixing container 1 will suck the monomer M out of the liquid containers 18 and through the cannulae 14 into the mixing space 4 and the polymer P therein.

If the liquid containers 18 are designed to be compressed by the pressure difference between the vacuum which through the connection with the mixing container 1 is generated therein, the liquid component M can be pressed out of said liquid containers 18 and through the cannulae 14 into the mixing space 4 of the mixing container 1 and the powder component P therein.

Thus, suction and/or pressing of the liquid component M to the powder component P may occur.

Since the cannulae 14 are located between the first and second end portions 33, 34 of the mixing container 1 and at a distance therefrom, the monomer M will reach the polymer P about "in the middle" thereof, which is advantageous since the monomer M hereby can spread or disperse quickly up- and downwards in the polymer powder. Since the liquid containers 18 can be compressed or rather contracted by suction by said vacuum, said containers 18 can be completely emptied.

This transfer of monomer M to polymer P is very quick and effective and when it is carried through, the empty liquid containers 18 may remain in their emptying positions.

Then, mixing is carried through under a vacuum and is performed by moving the mixing means 7 back and forth while at the same time rotating it relative to the mixing container 1.

After the mixing operation, the mixing means 7 is withdrawn as far as possible out of the mixing container 1 and this is concluded by rotating the mixing means 7 a few times for cleaning the filter 11.

After the mixing operation, collection is carried through also under a vacuum. Collection is performed by releasing the piston 13 from the mixing container 1, which means that said vacuum in the mixing space 4 sucks the piston 13 towards the second end portion 34 of the mixing container 1. The piston 13 will thereby bring along and collect the mixed bone cement in such a part 35 of the mixing space 4 which is located at the second end portion 34 and from which the bone cement shall be discharged.

Then, the mixing means 7 is broken off, the hose 9 loosened, the plug 12 screwed off and the discharge nozzle screwed onto the connecting member 8. Finally, the mixing container 1 is in a manner known per se positioned in a gun-like device (not shown) which permits discharge of bone cement from said part 35 of the mixing container 1 through the discharge nozzle by pressing the piston 13 towards the second end portion 34 of the mixing container 1.

The invention is not limited to the method described above or to the device described above and illustrated in the drawings. As methods and devices not described in detail one can mention production of something else than bone cement, wherein another liquid component than monomer and another powder component than polymer can be used. Furthermore, only one liquid container instead of two can be emptied into the mixing container, whereby it will suffice with one cannula. A vacuum in the mixing container can be generated by other means than a vacuum pump and the level of the negative pressure can be set as desired. The cannula can be designed in other ways provided it can be used for perforating the liquid container and the liquid component flows from said liquid container to the mixing container. The liquid containers can be located in the brackets on delivery of the device or they can alternatively be located in the brackets after delivery. Finally, it should be mentioned that the liquid containers can be of a bag-like type, but liquid containers of another material, e.g. glass, can also be used.

The invention claimed is:

1. Method for bringing a powder and a liquid component, in contact with each other for mixing thereof to form bone cement, wherein:
   the powder component (P) is placed in a mixing container (1) in which the mixing shall occur and the liquid component (M) in at least one liquid container (18) from which said liquid component (M) is transferred to the powder component (P) in the mixing container (1),
   a vacuum is generated in the mixing container (1),
   the liquid container (18) is opened by means of at least one cannula (14) through which the liquid component (M) can be brought to flow from the liquid container (18) to the mixing container (1), the cannula being located between a first and a second end portion (33, 34) of the mixing container (1) and protruding from said mixing container (1) in a radial direction relative to a geometric longitudinal axis (A) of the mixing container (1),
   the vacuum is brought to suck the liquid component (M) from the liquid container (18), through the cannula (14) and into the mixing container (1) to the powder component (P) therein, and/or
   the liquid component (M) is pressed into the mixing container (1) through the cannula (14) while the liquid container (18) is compressed because of the pressure difference between the vacuum in the interior of the liquid container (18) and the air pressure outside said liquid container.

2. Method according to claim 1, wherein a sealing means (25) is brought to provide sealing between the cannula (14) and the liquid container (18) and about such a wall portion (21) of the liquid container (18) which is opened by the cannula.

3. Method according to claim 1, wherein the liquid container (18) is opened by the cannula (14) by pressing said liquid container against said cannula.

4. Method according to claim 3, wherein the liquid container (18) is opened by pressing it against the cannula (14).

5. Method according to claim 1, wherein the liquid container (18) is placed in a ready position from which it is pressed in a direction towards the cannula (14) such that the liquid container (18) is opened thereby.

6. Method according to claim 5, wherein the liquid container (18) is held in the ready position by a bracket (23) and is pressed from said position towards the cannula (14) by pressing the bracket (23) in a direction towards said cannula.

7. Method according to claim 1, wherein the liquid container (18) is opened by bringing the cannula (14) to penetrate such a wall portion (21) of said liquid container (18) which closes a lateral hole (20) in an inner tube member (19) in the liquid container (18).

8. Method according to claim 1, wherein the liquid component (M) is sucked into the powder component (P) in the mixing container (1) at a side of said container situated between a first and a second end portion (33, 34) thereof.

9. Method according to claim 1, wherein the liquid component (M) is sucked out of two liquid containers (18) and into the mixing container (1), whereby one of the liquid containers (18) is opened by a first cannula (14) and the other liquid container (18) by another cannula (14).

10. Method according to claim 9, wherein the liquid containers (18) are opened substantially at the same time by being pressed substantially at the same time against the cannulae (14).

11. Method according to claim 1, wherein mixing of the powder and liquid components (P, M) is performed in the mixing container (1) while there is a vacuum therein.

12. Method according to claim 1, wherein mixing of the powder and liquid components (P, M) is performed in the mixing container (1) by means of a mixing means (7) therein.

13. Method according to claim 1, wherein:
the mixed mixture is collected in such a part (35) of the mixing container (1) from which the mixture shall be discharged, and the collection is carried through by means of a piston (13) which is released and sucked in a direction towards said part (35) of the mixing container (1) by being affected by a vacuum therein.

14. Method according to claim 1, wherein a vacuum is generated in the mixing container (1) corresponding to a negative pressure of about −0.87 bar.

15. Method according to claim 1, wherein the powder component (M) extends within the mixing container (1) from a first position along the longitudinal axis (A) to a second position along the longitudinal axis (A), the liquid component (M) being sucked into the mixing container (1) between the first position and the second position.

16. Method for bringing a powder and a liquid component in contact with each other for mixing thereof to form bone cement,
wherein the powder component (P) is placed in a mixing container (1) in which the mixing shall occur and the liquid component (M) in at least one liquid container (18) from which the liquid component (M) is transferred to the powder component (P) in the mixing container (1), wherein a vacuum is generated in the mixing container (1),
the liquid container (18) being opened by at least one cannula (14) member non-displaceably provided on the mixing container (1) and projecting from the mixing container in a radial direction relative to a geometric longitudinal axis (A) thereto, by pressing a bracket (23), by means of which the liquid container (18) is held in a ready position, laterally from the ready position towards the cannula, that a sealing means (25) is brought to provide sealing between the cannula (14) and the liquid container (18) and about such a wall portion (21) of the liquid container (18) which is opened by the cannula,
such that the vacuum in the mixing container (1) can suck the liquid component (M) from the liquid container (18), through the cannula (14) and into the mixing container (1) and the powder component (P) therein, and/or
such that the liquid component (M) is pressed into the mixing container (1) through the cannula (14) while the liquid container (18) is compressed because of the pressure difference between the vacuum in the interior of the liquid container (18) and the air pressure outside the liquid container, and
that mixing of the powder and liquid components (P, M) is performed in the mixing container (1) while there is a vacuum therein.

17. Method according to claim 16, wherein the liquid container (18) is opened by pressing it against a cannula (14) which is located on the mixing container (1) between a first and a second end portion (33, 34) thereof.

18. Method according claim 16, wherein the liquid container (18) is opened by bringing the cannula (14) to penetrate such a wall portion (21) of the liquid container (18) which closes a lateral hole (20) in an inner tube member (19) in the liquid container (18).

19. Method according claim 16, wherein the liquid component (M) is sucked into the powder component (P) in the mixing container (1) at a side of the container situated between a first and a second end portion (33, 34) thereof.

20. Method according claim 16, wherein the liquid component (M) is sucked out of two liquid containers (18) and into the mixing container (1), whereby one of the liquid containers (18) is opened by a first cannula (14) and the other liquid container (18) by another cannula (14).

21. Method according to claim 20, wherein the liquid containers (18) are opened substantially at the same time by being pressed substantially at the same time against the cannula (14).

22. Method according claim 16, wherein mixing of the powder and liquid components (P, M) is performed in the mixing container (1) by means of a mixing means (7) therein.

23. Method according claim 16, wherein the mixed mixture is collected in such a part (35) of the mixing container (1) from which the mixture shall be discharged, and that this collection is carried through by means of a piston (13) which is released and sucked in a direction towards the part (35) of the mixing container (1) by being affected by a vacuum therein.

24. Method according claim 16, wherein a vacuum is generated in the mixing container (1) corresponding to a negative pressure of about −0.87 bar.

* * * * *